United States Patent
Roby et al.

(10) Patent No.: US 6,644,093 B2
(45) Date of Patent: Nov. 11, 2003

(54) FRAY TESTER

(75) Inventors: Mark S. Roby, Killingworth, CT (US); John J. Kennedy, Guilford, CT (US); Frank Leonard, Northford, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 10/079,396

(22) Filed: Feb. 19, 2002

(65) Prior Publication Data

US 2002/0173740 A1 Nov. 21, 2002

Related U.S. Application Data

(60) Provisional application No. 60/278,686, filed on Mar. 26, 2001.

(51) Int. Cl.[7] .................................................. G01N 3/56
(52) U.S. Cl. ....................................... 73/7; 73/9; 73/159
(58) Field of Search .......................... 73/7, 9, 158, 159, 73/160

(56) References Cited

U.S. PATENT DOCUMENTS

| 1,436,323 | A | | 11/1922 | Schnable et al. ................. 73/7 |
| 2,018,971 | A | | 10/1935 | Paume ............................. 73/7 |
| 2,397,227 | A | | 3/1946 | Wilhoyte, Jr. ..................... 73/7 |
| 2,910,863 | A | | 11/1959 | Hornbostel et al. ............ 73/86 |
| 3,209,589 | A | * | 10/1965 | Schlatter ...................... 73/160 |
| 3,726,137 | A | * | 4/1973 | Denton ........................ 73/160 |
| 3,942,532 | A | * | 3/1976 | Hunter et al. ................ 606/231 |
| 4,027,676 | A | * | 6/1977 | Mattei ......................... 606/230 |
| 4,983,180 | A | * | 1/1991 | Kawai et al. ................ 606/230 |
| 5,584,858 | A | | 12/1996 | Totakura ...................... 606/228 |
| 5,635,124 | A | * | 6/1997 | Abrams et al. ............. 264/257 |
| 5,939,191 | A | | 8/1999 | Bennett et al. ............. 428/375 |

* cited by examiner

*Primary Examiner*—Hezron Williams
*Assistant Examiner*—David Rogers

(57) ABSTRACT

A fray tester for evaluating fray resistance of surgical sutures is provided, which comprises a first and a second pulley rotatably adapted in a spaced relation to each other, a tensioning weight, and a reciprocity driver. A suture having a first end portion, a second end portion and an intermediate portion is mounted in the fray tester such that the first end portion is subject to the tensioning weight, the intermediate portion is mounted to the first and second pulleys and defines a wrapped portion, the second end portion being connected to the reciprocating driver to cause the suture to rub against itself at a wrapped portion. The reciprocating driver includes a rotating wheel connected to a motor for providing the reciprocating movement to the suture to be tested. The tester may further include a revolution counter for counting and displaying the number of reciprocating cycles at the time the suture breaks or seizes.

23 Claims, 4 Drawing Sheets

FRAY TESTER

This application claims the benefit of Provisional application Ser. No. 60/278,686, filed Mar. 26, 2001.

BACKGROUND

1. Technical Field

The present disclosure generally relates to a fray tester for sutures. In particular, the disclosure relates to a test apparatus and related methods for evaluating fray resistance or break-down performance of a surgical suture when rubbing against itself.

2. Background of the Related Art

Sutures are often used in surgical procedures for holding cut tissue surfaces in apposition for a period of time sufficient for healing. Non-absorbable sutures, e.g. sutures made from non-bioabsorbable materials such as polyolefins, nylon, cotton, and the like, are generally removed after a period of time. Absorbable sutures, e.g. those fabricated from bioabsorbable materials such polymers of lactide and glycolide, collagen, and the like, are gradually degraded and absorbed by the body, and do not require subsequent removal.

A suture having a good degree of flexibility and pliability can conform closely to body tissue without undue pressure. Good flexibility and pliability enhance the degree to which a suture can be tied down, knotted and securely placed in a desired position. Various attempts have been made to modify and optimize the physical characteristics of gut sutures. For example, various suture coatings and tubing fluids-have been developed to achieve or enhance flexibility and pliability, and also to improve the handling characteristics of sutures, such as fray resistance or run-down performance.

In addition to the research efforts on suture materials, coatings and tubing fluids, several testing techniques have been adopted for evaluating such handling characteristics of sutures.

An example of a fray resistance test is described in U.S. Pat. No. 5,584,858. Such fray tester utilizes a static suture wound around rollers, and a dynamic suture wrapped twice at a point around the static suture with a weight attached at one end of the dynamic suture, the dynamic suture being subject to rubbing cycle against the static suture until the sutures break to stop the test.

SUMMARY

The present disclosure is directed to a fray tester for evaluating fray resistance characteristics of surgical sutures. Simulating real surgical operations where the surgeon repeatedly knots the suture, the fray tester is adapted to provide repeated rubbing action at a wrapped portion of the suture while counting the number of such rubbing cycles until the suture seizes or breaks down.

The fray tester comprises first and second pulleys rotatably adapted in a spaced relation to each other, a tensioning weight, and a reciprocating driver. In operation, a suture having a first end portion, a second end portion and an intermediate portion is mounted in the tester with the second end portion being subject to the tensioning weight, the intermediate portion mounted around the first and second pulleys and defining a wrapped portion, the first end portion being connected to the reciprocating driver which causes the intermediate portion of the suture to rub against itself at the wrapped portion.

In a preferred embodiment, the reciprocating driver is a rotating wheel connected to a motor for providing the reciprocating movement to the suture to be tested. The tester may further include a revolution counter for counting and displaying the number of cycles at the time the suture breaks, seizes or reaches some predetermined state of degradation.

BRIEF DESCRIPTION OF THE DRAWINGS

Preferred embodiments of the disclosure are described herein with reference to the drawings, wherein.

DETAILED DESCRIPTION OF PREFERRED EMBODIMENTS

Figure 1:
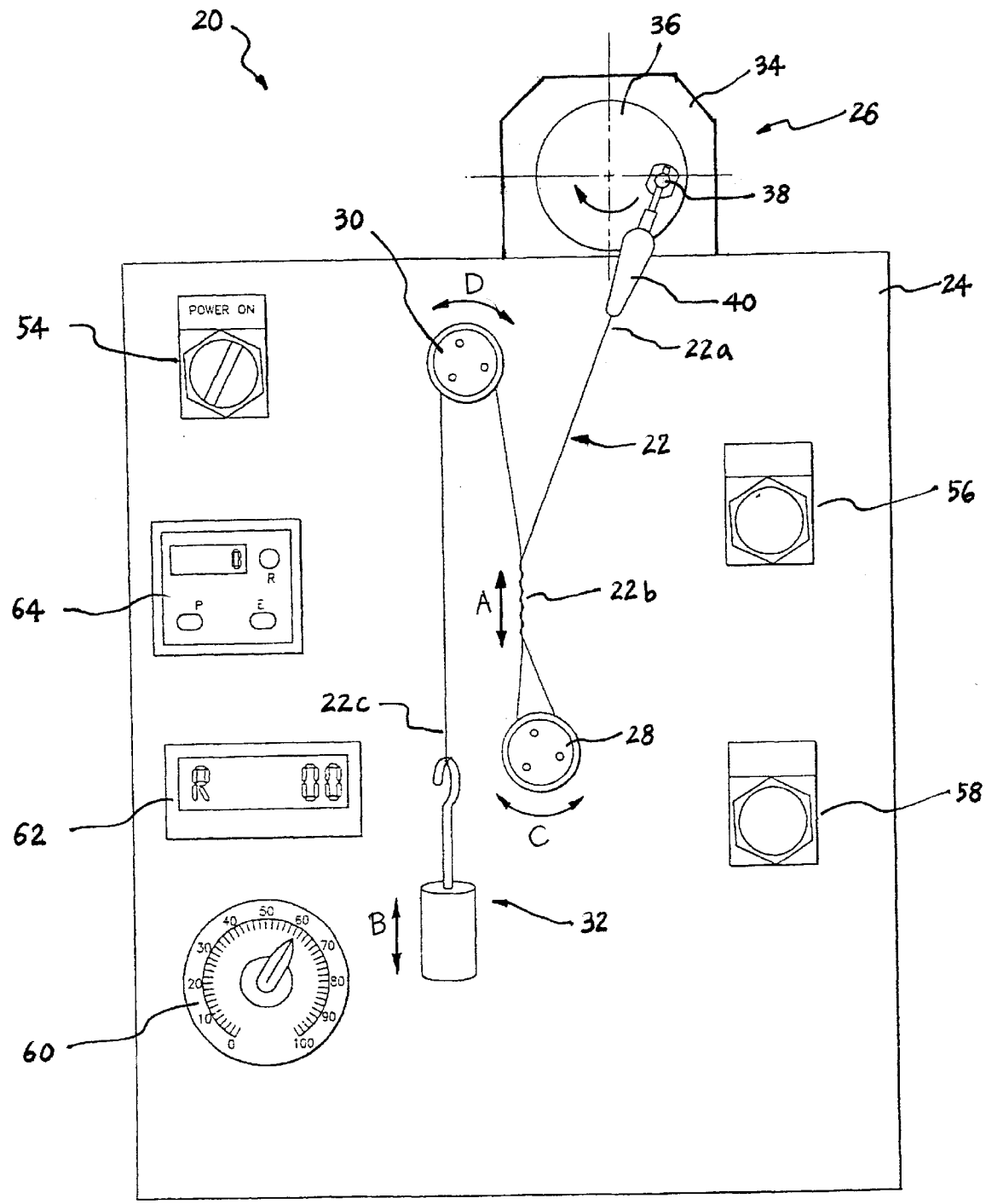
FIG. 1 is a front elevational view of a fray tester of the invention.

Referring now to the drawings in detail, FIG. 1 illustrates a fray tester, generally referred to by reference numeral 20, for measuring and evaluating fray resistance properties of a surgical suture 22 installed thereon as described hereinafter.

Fray tester 20 includes a frame 24, a reciprocating driver 26, first and second pulleys 28 and 30 spaced vertically apart and rotatably mounted on the frame 24, and a tensioning weight 32 to apply appropriate tension to the suture 22 during the fray resistance test. The first and second pulleys each include a center groove around the perimeter for wrapping the suture therearound, and a suitable bearing for providing free revolution to the pulley in either direction. In a preferred embodiment, the diameter of the center groove of each pulley is about 0.6 inches, and the vertical distance between the centers of the two pulleys is about 6 inches. However, it is to be noted that the size of each pulley and the distance between them may be varied according to the particular design of the tester.

Reciprocating driver 26 preferably includes a motor 34 positioned adjacent the frame 24, a rotating wheel 36, a gripper post 38 attached to the rotating wheel 36 and a gripper 40 for holding a first end 22a of the suture 22.

Figure 2:
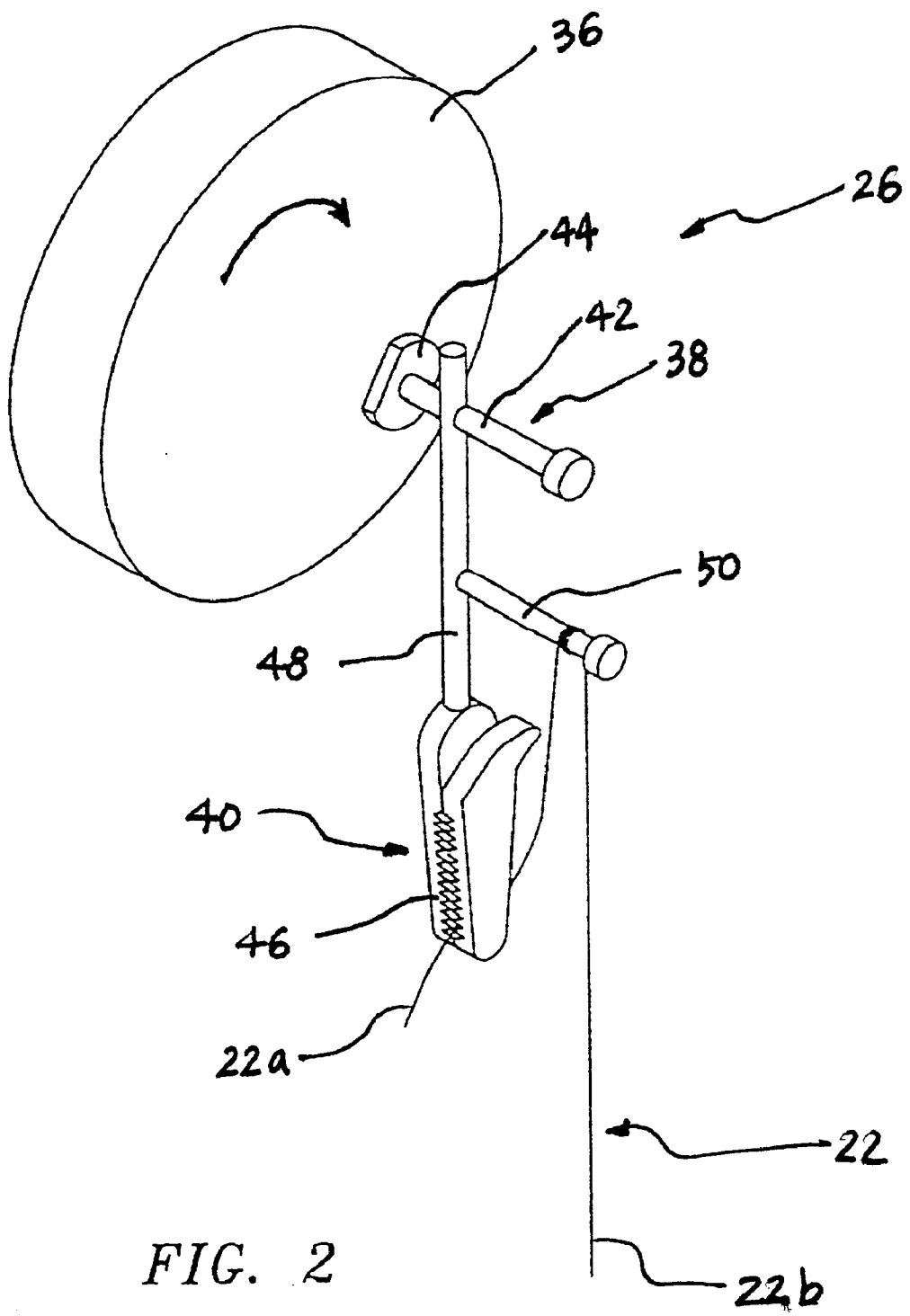
FIG. 2 is a perspective view illustrating reciprocating driver with the suture installed thereon.

As shown in FIG. 2, gripper post 38 includes a shaft portion 42 and a mounting portion 44 for respectively connecting with the gripper 40 and the rotating wheel 36. Preferably, the mounting portion 44 is freely rotatable relative to the rotating wheel 36 in order to maintain the pointing direction of the gripper 40 substantially toward a wrapped portion 22b of the suture. Gripper 40 may include a clip 46 of known type for clamping the suture, a clip post 48 for connecting the clip 46 with the gripper post 38, and a suture winding post 50 for assisting holding of the suture without slippage. Other types of reciprocating drivers for moving the suture relative to itself, including conventional driving mechanisms and suture gripping mechanisms, may be contemplated by the person ordinarily skilled in the art without substantially differing from the concept and principles of the present invention.

Fray tester 20 further includes power switch 54, start button 56 and stop button 58 for starting and stopping the reciprocating motion of the reciprocating driver 26, RPM setting knob 60 for presetting the rotation speed of wheel 36, RPM indicator 62 for displaying such rotation speed, and rotation counter 64 for counting actual revolution of the rotating wheel 36 in real time. Fray tester 20 also includes seizure/break-down detector which is described in detail below.

Referring to FIGS. 1 and 2, installation of the suture for the fray test according to a preferable embodiment is described. A suture 22 to be tested is cut to an appropriate length, preferably 24 inches or longer. Then, the location of gripper post 38 relative to the rotating wheel 36 is positioned between the top right position and 6 o'clock position by jogging the start button 56. A first end portion 22a of the suture 22 is then mounted to the gripping mechanism of the tester, preferably in the following manner. First, leaving about two inches from the end of the suture 22, the suture is wrapped around the suture winding post 50 several times, for example three wraps. Then, while holding the long portion of the suture, the first end portion 22a of the suture is inserted into and grasped by the jaw portions of the clip 46 as shown in FIG. 2. Next, guiding the long end of the suture to the lower pulley 28 (FIG. 1), the suture 22 is placed around the center groove of the pulley 28 and brought up vertically making, for example, about a three hundred (300) degree wrap around the pulley 28. Now, while pulling the suture 22 upward, the intermediate portion 22b of the suture is wrapped by a predetermined number of times, preferably 5 times for conventional size 5/0 sutures. Then, the long end 22c of the suture is guided over the upper wheel 30 making about a 300 degree wrap around the wheel 30. Now, a weight 32 is hung at the end portion 22c of the suture using an adequate loop portion made thereof, to provide an adequate tension to the suture for the test. The weight 32 is preferably of fifty (50) gram weight for conventional size 5/0 sutures. The actual weight of the weight 32 and the number of wraps in the intermediate portion 22b of the suture 22 may differ depending on the suture materials, the size of the suture, and/or the adopted testing procedure.

Figure 4:
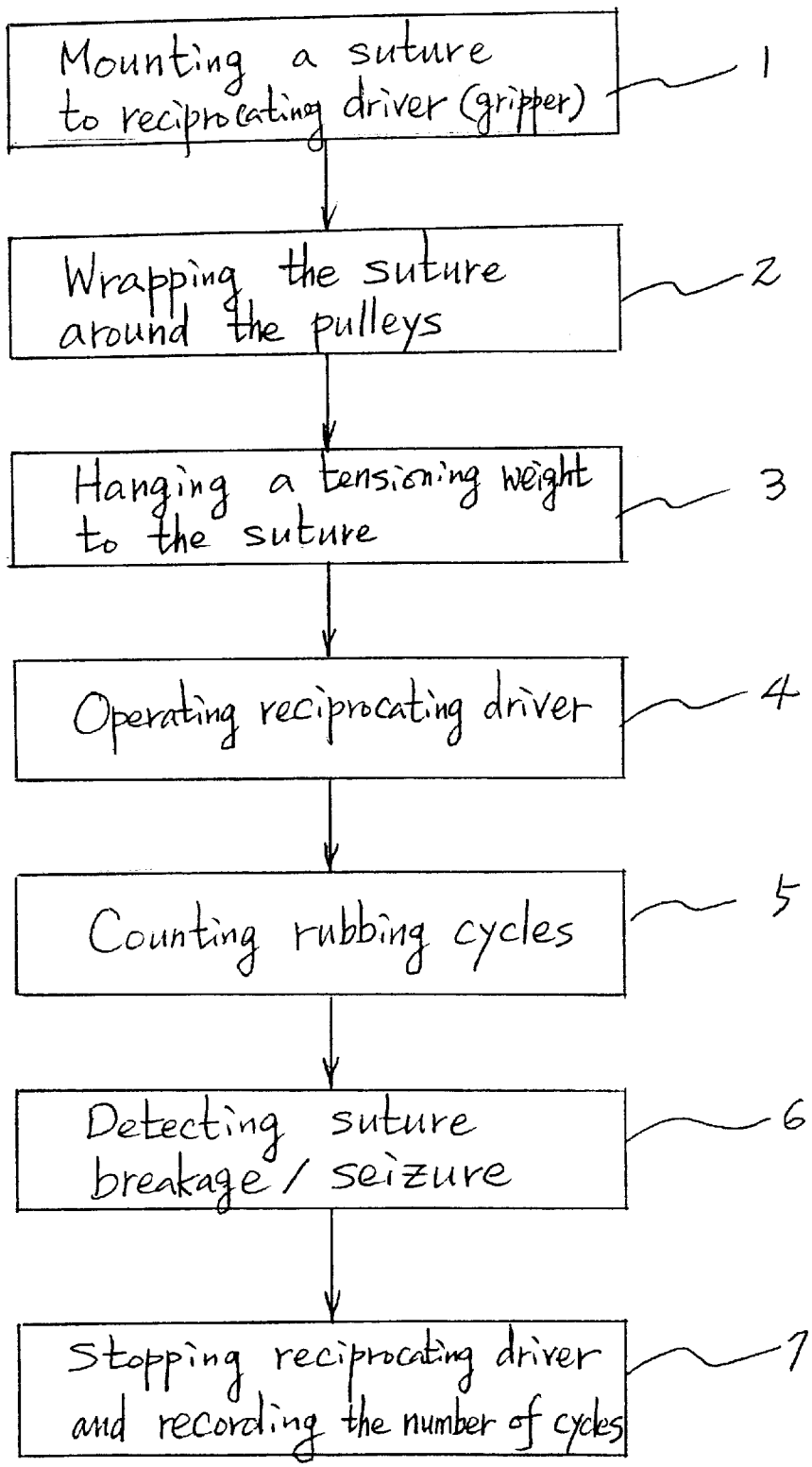
FIG. 4 is a flow chart illustrating major steps of the testing procedure of the invention.

Steps 1 to 3 in FIG. 4 summarizes the major steps of the installation process described above.

Figure 3:
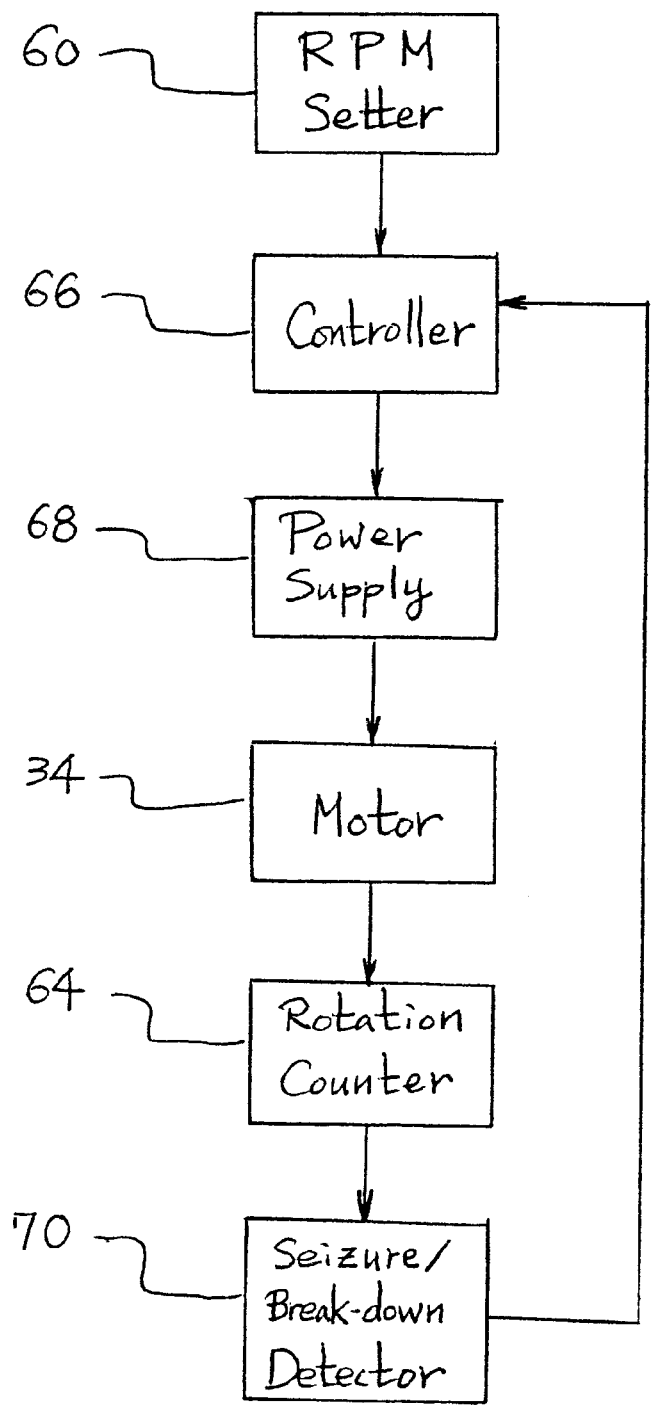
FIG. 3 is a schematic block diagram of one embodiment of the control system associated with the fray tester.

With reference to FIGS. 1 and 3, operation of the test procedure is described.

After installing the suture 22 to the tester 20 as described above, power switch 54 is set to the on-position, the proper RPM is set by RPM setter 60, and rotation counter 64 is reset to zero. The range of RPM is preferably between about 25 and 60, more preferably between 40 and 50.

Now, by pushing the start button 56, the fray tester 20 starts its testing operation. A suitable controller 66 controls operation of motor 34 through power supply 68, and of other components of the tester 20. Rotation counter 64 is connected to the motor 34 and count the rotation of the motor in real time. As shown in FIG. 1, rotation of the motor 34 provides reciprocating action to the first end 22a of the suture 22. This reciprocating action causes the suture 22, including the wrapped portion 22b, and the weight 32 to move up and down as indicated by the double headed arrows A and B. In order to facilitate the reciprocating movement of the suture, the first and second pulleys 28 and 30 are subject to subordinate rotational movement to back and forth directions as indicated by the arrows C and D. Thus, rotation of the motor 34 makes the suture 22 rub against itself at the wrapped portion 22b while suitable tension is applied to the suture 22 by the weight 32.

Upon repeated rubbing action, the wrapped portion of the suture becomes fragile and breaks or seizes. Seizure/breakdown detector 70 is provided to detect such breaking, seizure or degradation of the suture and send the corresponding signal to the controller 66 to stop running of the motor 34. For detecting such seizure or breakdown of the suture, various detecting or sensing means can be utilized. For example, a tension detector of known type may be disposed adjacent the gripper post 38 for detecting the change in tension occurring at the suture 22 when it breaks, seizes or reaches to the point that the tension exceeds a predetermined amount because of progress of fray in the suture. Alternatively, a torque detector may be connected to the motor 34 to detect the change in torque when the above-mentioned occurrence happens.

Consequently, upon stopping of the motor, revolution counter 64 displays the number of actual revolution of the motor or the rotating wheel (i.e., the number of rubbing cycles) at the time the suture breaks or seizes.

In addition to the suture installation process, steps 4 to 7 in FIG. 4 summarizes the major steps of the testing process described above.

By way of example, Table I below shows a sample result of the fray resistance test, where the RPM of the fray tester was set to 44 revolutions per minute, size 5/0 suture samples were wrapped five times and a fifty gram weight was applied. The suture samples were of conventional commercial production.

TABLE I

| Gut Suture Sample | Cycles to fail |
| --- | --- |
| Polypropylene | 465 |
| Hytrel coated with a random copolymer of 50% caprilactone, 41% PLURONIC and 9% glycolide | 1500 |
| Polyhexofluoropropylene | 214 |
| Nylon | 1000 + (Fray did not occur.) |

While the above description contains many specifics, these specifics should not be construed as limitations on the scope of the disclosure, but merely as exemplifications of preferred embodiments thereof. For example, it is envisioned that the first and the second pulleys are preferably positioned on the frame in a substantially vertical relation to each other, as shown in FIG. 1. However, they may be disposed in other positional relation, such as in substantial oblique relation or even in horizontal relation to each other. Those skilled in the art will envision many other possible variations that are within the scope and spirit of the disclosure as defined by the claims appended hereto.

What is claimed is:

1. A fray tester for evaluating fray resistance of a suture, comprising:

first and second pulleys rotatably adapted in a spaced relation to each other;

a tensioning weight; and a rotatably adapted reciprocating driver for providing reciprocating motion to a suture wrapped around said first and second pulleys.

2. The fray tester of claim 1 further including a counter for counting the number of cycles of the reciprocating movement until a suture mounted in said fray tester fails.

3. The fray tester of claim 1 further including a speed control for setting the speed of the reciprocating driver.

4. An apparatus for evaluating fray resistance of a suture, comprising:

first and second pulleys rotatably adapted in a spaced relation to each other;

a tensioning weight; and a reciprocating driver including a rotating wheel for providing reciprocating motion to a suture wrapped around said first and second pulleys.

5. The fray tester of claim 4 further including a suture gripper mounted to the rotating wheel.

6. A method of testing fray resistance of a suture, comprising the steps of:
   providing a fray tester including first and second pulleys rotatably adapted in a spaced relation to each other, a tensioning weight, and a rotatably adapted reciprocating driver;
   providing a suture including a first end portion, a second end portion and an intermediate portion;
   mounting the first end portion of the suture to the reciprocating driver;
   wrapping the intermediate portion of the suture around the first and second pulleys while defining a wrapped portion therein;
   hanging the tensioning weight to the second end portion of the suture;
   operating the reciprocating driver, and thereby providing reciprocating motion to the suture and causing the suture to repeatedly rub against itself; and
   counting the number of rubbing cycles until the suture breaks, seizes or reaches a predetermined state of degradation.

7. The method of claim 6 further including the step of detecting when the suture fails.

8. The method of claim 6 further including the step of displaying the number of rubbing cycles when the suture fails.

9. The method of claim 6, wherein the reciprocating driver includes a suture gripper connected to the reciprocating driver, and the step of mounting is performed by mounting the first end portion of the suture to the suture gripper.

10. An apparatus for evaluating fray resistance of a suture, comprising:
    first and second pulleys rotatably adapted in a spaced relation to each other;
    a tensioning weight attachable to an end portion of a suture; and
    a reciprocating driver including a rotating wheel for providing reciprocating motion to said suture wrapped around said first and second pulleys.

11. The apparatus of claim 10, further including a suture gripper mounted to the rotating wheel.

12. The apparatus of claim 10, further including a counter for counting the number of cycles of the reciprocating movement until a suture mounted in said fray tester fails.

13. The apparatus of claim 10, further including a speed control for setting the speed of the rotating wheel.

14. A method of testing fray resistance of a suture, comprising the steps of:
    providing a fray tester including first and second pulleys rotatably adapted in a spaced relation to each other, a tensioning weight, and a rotating driver;
    providing a suture including a first end portion, a second end portion, and an intermediate portion;
    mounting the first end portion of the suture to the rotating driver;
    wrapping the intermediate portion of the suture around the first and second pulleys while defining a wrapped portion therein;
    hanging the tensioning weight to the second end portion of the suture;
    operating the rotating driver, and thereby providing reciprocating motion to the suture and causing the intermediate portion of the suture to repeatedly rub against itself; and
    counting the number of rubbing cycles until the suture fails.

15. The method of claim 14, wherein the step of operating the rotating driver further includes providing a rotating wheel attached to said first end portion of the suture for providing the reciprocating motion.

16. The method of claim 14, further including the step of detecting when the suture fails.

17. The method of claim 14, further including the step of displaying the number of rubbing cycles when the suture fails.

18. The method of claim 14, wherein the rotating driver includes a suture gripper connected to the rotating driver, and the step of mounting is performed by mounting the first end portion of the suture to the suture gripper.

19. An apparatus for evaluating fray resistance of a suture, comprising:
    first and second pulleys rotatably adapted in a spaced relation to each other;
    a tensioning weight attachable to an end portion of a suture; and
    a rotating driver for providing reciprocating motion to a suture wrapped around said first and second pulleys.

20. The fray tester of claim 19, wherein the rotating driver includes a rotating wheel for providing the reciprocating movement to the suture.

21. The fray tester of claim 20, further including a suture gripper mounted to the rotating wheel.

22. The fray tester of claim 19, further including a counter for counting the number of cycles of the reciprocating movement until a suture mounted in said fray tester fails.

23. The fray tester of claim 19, further including a speed control for setting the speed of the reciprocating driver.

* * * * *